(12) United States Patent
Hong et al.

(10) Patent No.: US 9,579,191 B2
(45) Date of Patent: Feb. 28, 2017

(54) OPTICAL STRUCTURES WITH NANOSTRUCTRE FEATURES AND METHODS OF USE AND MANUFACTURE

(75) Inventors: Xin Hong, Fort Worth, TX (US); David Meadows, Colleyville, TX (US); Qiwen Zhan, Mason, OH (US); Mutlu Karakelle, Fort Worth, TX (US)

(73) Assignee: Novartis AG, Basel (CH)

( * ) Notice: Subject to any disclaimer, the term of this patent is extended or adjusted under 35 U.S.C. 154(b) by 536 days.

(21) Appl. No.: 13/439,080

(22) Filed: Apr. 4, 2012

(65) Prior Publication Data

US 2012/0259411 A1   Oct. 11, 2012

Related U.S. Application Data

(60) Provisional application No. 61/472,948, filed on Apr. 7, 2011.

(51) Int. Cl.

| | |
|---|---|
| *A61F 2/16* | (2006.01) |
| *G02B 1/115* | (2015.01) |
| *A61F 2/00* | (2006.01) |
| *G02B 1/118* | (2015.01) |
| *B82Y 20/00* | (2011.01) |
| *G02C 7/04* | (2006.01) |

(52) U.S. Cl.
CPC .............. *A61F 2/16* (2013.01); *A61F 2/0077* (2013.01); *B82Y 20/00* (2013.01); *G02B 1/115* (2013.01); *G02B 1/118* (2013.01); *G02C 7/049* (2013.01); *A61F 2002/1696* (2015.04); *A61F 2002/1699* (2015.04); *G02B 2207/101* (2013.01); *G02C 7/04* (2013.01)

(58) Field of Classification Search
CPC .. A61F 2/14; A61F 2/16; A61F 2/0077; A61F 2002/1697; A61F 2002/1696; G02B 1/115; G02B 1/118
See application file for complete search history.

(56) References Cited

U.S. PATENT DOCUMENTS

| | | | |
|---|---|---|---|
| 4,013,465 A | 3/1977 | Clapham et al. | |
| 7,061,693 B2 | 6/2006 | Zalevsky | |
| 7,438,411 B2 | 10/2008 | Payne et al. | |
| 7,658,991 B2 | 2/2010 | Zhao et al. | |
| 7,789,910 B2* | 9/2010 | Knox et al. | 623/6.56 |
| 7,842,086 B2 | 11/2010 | Dotan et al. | |
| 2003/0214060 A1 | 11/2003 | Wires | |
| 2006/0215280 A1 | 9/2006 | Hayashi et al. | |
| 2009/0169859 A1 | 7/2009 | Biteau et al. | |

(Continued)

FOREIGN PATENT DOCUMENTS

| | | |
|---|---|---|
| EP | 0242043 | 10/1987 |
| EP | 1690513 | 8/2006 |

(Continued)

OTHER PUBLICATIONS

International Search Report and Written Opinion issued for PCT/US2012/032088, dated Jul. 26, 2012, 8 pgs.

(Continued)

*Primary Examiner* — Howie Matthews

(57) ABSTRACT

An ophthalmic lens system comprises a lens body with a curved outer surface and an assembly including a plurality of spaced apart nanostructures. The assembly covers at least a portion of the curved outer surface.

25 Claims, 6 Drawing Sheets

(56) References Cited

U.S. PATENT DOCUMENTS

| | | | |
|---|---|---|---|
| 2010/0053549 | A1 | 3/2010 | Legerton et al. |
| 2010/0118407 | A1 | 5/2010 | Huff |
| 2010/0166983 | A1 | 7/2010 | Cho et al. |
| 2010/0196435 | A1* | 8/2010 | Freeman et al. ............. 424/423 |
| 2010/0261001 | A1 | 10/2010 | Chang et al. |
| 2011/0040376 | A1 | 2/2011 | Christie et al. |

FOREIGN PATENT DOCUMENTS

| | | |
|---|---|---|
| JP | S50-070040 | 6/1975 |
| JP | S62-221345 | 9/1987 |
| JP | 2000-056115 | 2/2000 |
| JP | 2003-275230 | 9/2003 |
| JP | 2006-187635 | 7/2006 |
| JP | 2006-267624 | 10/2006 |
| JP | 2007-090656 | 4/2007 |
| JP | 2010-533876 | 10/2010 |
| WO | WO 2009/012141 | 1/2009 |

OTHER PUBLICATIONS

Extended European Search Report and Annex to the European Search Report issued for EP Application No. 12770533 dated Feb. 16, 2015, 5 pgs.

English Translation of Japanese Office Action issued for JP 2014-503933 dated Feb. 19, 2015 (mailing date of Feb. 24, 2015), 4 pgs.

Australian Office Action issued for Australian Application No. 2012243101 dated Jun. 24, 2016 (mailing date of Jul. 5, 2016), 5 pgs.

* cited by examiner

OPTICAL STRUCTURES WITH NANOSTRUCTRE FEATURES AND METHODS OF USE AND MANUFACTURE

RELATED APPLICATION

This application claims priority to U.S. provisional application Ser. No. 61/472,948, filed on Apr. 7, 2011, the contents which are incorporated herein by reference.

TECHNICAL FIELD

This disclosure relates in general to ophthalmic lenses and more particularly to ophthalmic lenses that have nanostructured thin film surfaces that reduce surface reflection.

BACKGROUND

Age, disease, trauma, or a combination thereof may result in deterioration in vision which may be corrected through the use of ophthalmic lenses. Ophthalmic lenses may include lenses positioned externally of the eye or implanted in the eye. Lenses positioned externally of the eye include spectacle lenses and contact lenses. Implanted lenses include intraocular lenses ("IOLs"). An "aphakic IOL" may be used to replace a natural lens of any eye that has, for example, developed a cataract. A "phakic IOL" is generally used with the natural lens intact. The phakic IOL may be located in either the anterior chamber (i.e., in front of the natural lens and the iris) or the posterior chamber (i.e., in front of the natural lens, but behind the iris).

Traditionally, the surface reflectance and scattering of light caused by ophthalmic lenses has been considered undesirable. For example, the reflectance may be cosmetically undesirable for persons who are on camera or photographed. Reflectance may also interfere with the physical examination of the eye. Some lens wearers also report glare, halos, dysphotopsia, reflections, and other undesirable images associated with reflective lenses.

Traditional anti-reflection coatings formed of uniform and polished anti-reflection layers have shortcomings. For example, the ability to reduce reflection may be limited by the available material's refractive index. Traditional coatings often require multiple layers and work only for a limited range of reflection angles. Additionally, traditional coatings often use rigid materials that interact poorly with biological tissue.

Accordingly, new systems and methods are needed to reduce reflection associated with ophthalmic lenses.

SUMMARY

In one exemplary aspect, an ophthalmic lens system comprises a lens body with a curved outer surface and an assembly including a plurality of spaced apart nanostructures. The assembly covers at least a portion of the curved outer surface.

In another exemplary aspect, a method of forming an ophthalmic lens comprises providing a lens body with a curved outer surface and modifying at least a portion of the curved outer surface to include first assembly including a plurality of spaced apart nanostructures. The first assembly covers at least a portion of the curved outer surface.

Further aspects, forms, embodiments, objects, features, benefits, and advantages of the present invention shall become apparent from the detailed drawings and descriptions provided herein.

BRIEF DESCRIPTION OF THE DRAWINGS

In the accompanying drawings, which are incorporated in and constitute a part of the specification, embodiments of the invention are illustrated, which, together with a general description of the invention given above, and the detailed description given below, serve to exemplify the embodiments of this invention.

DETAILED DESCRIPTION

Figure 1:
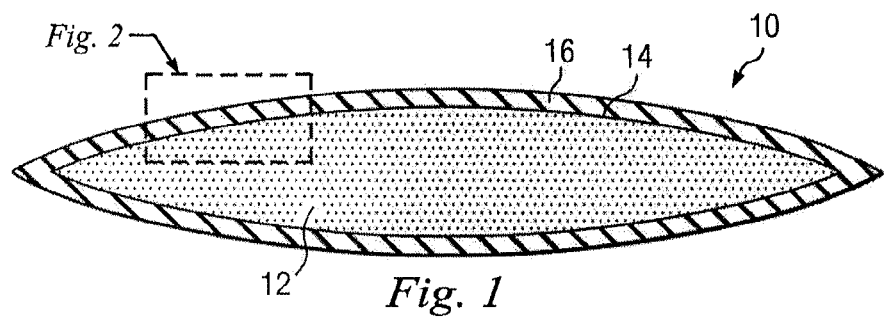
FIG. 1 is an ophthalmic lens with a nanostructure assembly.

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Figure 2:
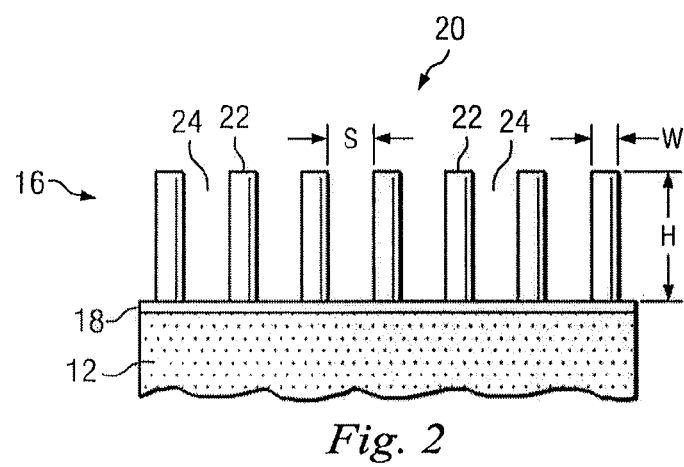
FIG. 2 is a close-up section of the lens of FIG. 1.

FIGS. 1 and 2 show an ophthalmic lens 10 with a lens body 12 with a curved surface 14. An nanostructure formation or assembly 16 is formed on the curved surface 14 of the lens body 12. As shown in the detailed view of FIG. 2, the nanostructure assembly 16 comprises a substrate 18 upon which nanostructures 20 are formed. The nanostructures 20 include protrusions 22 and interstices or spacings 24. The shape, size, angle, density, and material properties of the nanostructures may be designed to modify the effective refractive index of the lens 10, and thereby modify the reflectance of the lens. Designing the nanostructures with interstices to create a porous assembly 16 may result in the assembly having a lower refractive index than the material would have if deposited as a uniform layer. The porous assembly created by the nanostructures may further serve to reduce surface reflection, reduce surface scattering, improve biological tissue interaction, improve surface lubrication, and reduce or prevent posterior capsular opacification. As will be described in greater detail below, in some embodiments, multiple layers of the porous assembly 16 may be used increase reflectivity or create a multi-layer mirror.

In this embodiment, the protrusions 22 have an approximate height H between 100 and 200 nm and an approximate width W between 25 and 50 nm. The spacings 24 between the protrusions 22 have an approximate width S between 10 and 30 nm. It is understood that these dimensions are meant to be examples and dimensions greater or less than the dimensions listed may also be suitable. Through a combination of the shape, size, angle, density, and material properties of protrusions 22 and the shape, size, and density of the interstices 24, the assembly 16 may be formed to have a lower index of refraction than the lens body 12, thus reducing the amount of reflection caused by the lens 10 compared to the lens body 12 without the assembly 16. In at least one embodiment, the index of refraction of the assembly 16 may be less than 1.4 where the index of the unmodified lens body would otherwise range from about 1.52 to about 1.60. In other embodiments, the refractive index of the assembly may be between approximately 1.30 and 1.60.

The nanostructures may serve to reduce the reflectivity of the lens as compared to a lens without the nanostructures. For example intra ocular lenses in an aqueous environment may have a reflectivity of approximately 0.6%. A contact lens in an air environment may have a reflectivity approximately in the range of 2.5 to 5.5%. The incorporation of nanostructures, such as those described above and below, may serve to reduce the reflectivity.

In this embodiment, the anti-reflective assembly is shown to cover the entire curved surface 14, but in alternative embodiments, the anti-reflective assembly may be applied to discrete regions and omitted in other regions. In this embodiment, the curved surface is a convex surface, but in alternative embodiments, the surface of the lens body that receives the anti-reflective assembly may be convex, flat, or have a varied shape. Also in alternative embodiments, the anti-reflective assembly may be formed inside the lens body. For the purposes of this disclosure, the term "anti-reflective" may mean "non-reflective" or any level of reflectivity less than the lens body would have alone. In some alternative embodiments, the substrate may be the lens body itself, but in other embodiments, the substrate may be a separate material that is applied to the lens body.

Figure 3:
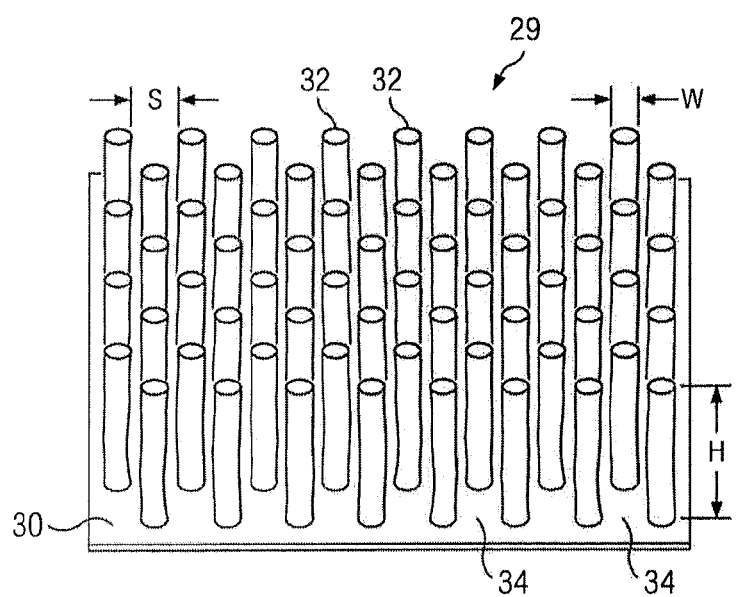
FIG. 3 an image of a nanostructure assembly according to one embodiment.

Referring now to FIG. 3, in one embodiment, the assembly 16 may be a nanoporous film 29 with a substrate 30 from which generally discrete rods 32 extend. The substrate may be, for example, a lens body. The rods 32 are separated by spacings or pores 34. The rods may have a height H between approximately 100 and 200 nm and a width W between approximately 25 and 50 nm. The pores may have a width S of approximately 20 nm.

The nanoporous film of this embodiment may be fabricated with controllable size ranges using any of a variety of techniques including physical vapor deposition, thermal evaporation, chemical vapor deposition, or etching. Suitable methods of physical vapor deposition may be performed by sputtering or energetic electron beam (E-beam evaporation). Suitable methods of chemical vapor deposition may include plasma enhanced chemical vapor deposition (PECVD). The rods may be formed from any of a variety of materials including dielectrics, metals, polymers, and organic materials. Silicon dioxide ($SiO_2$) is an example of a material that may be suitable.

Figure 4:
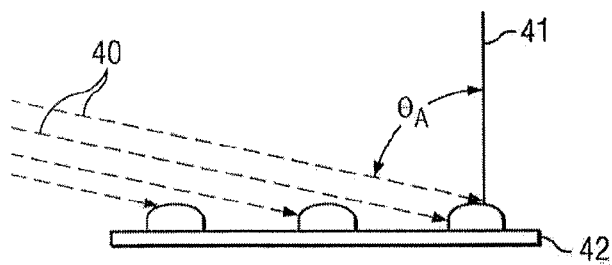
FIGS. 4-5 depict the formation of the nanostructure assembly of FIG. 3.
Figure 5:
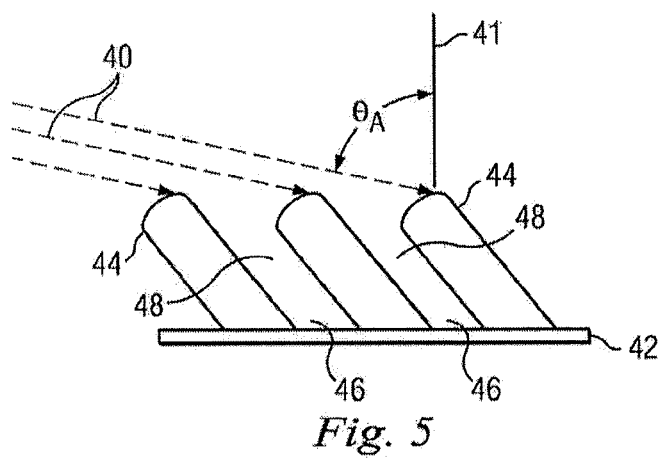

FIGS. 4-5 illustrate an example of a suitable oblique angle evaporation process for fabricating a nanoporous film of the type depicted in FIG. 3. As shown in FIG. 4, vapor flux 40 is applied at a vapor incident angle $\theta_A$ relative to an imaginary line 41 extending perpendicular to a substrate 42. As the vapor flux 40 is deposited, rods 44 are grown. The growing rods 44 produce shadow regions 46 where the vapor flux cannot be deposited. These regions 46 form the pores 48 between the rods 44. The porosity can be adjusted by adjusting the incident angle $\theta_A$ of the vapor flux. The process may directly modify the lens body substrate or the process may be performed on a separate substrate and later adhered to the lens body.

Figure 6:
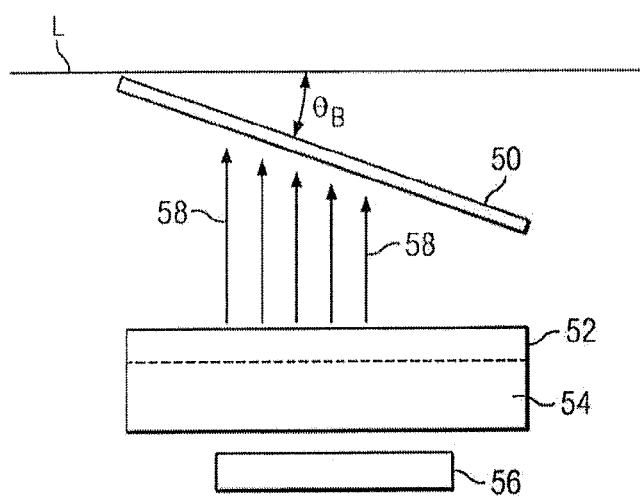
FIG. 6 is a fabrication set-up for forming the nanostructure assembly of FIG. 3.

As shown in FIG. 6, oblique angle e-beam evaporation is one method that may be used for oblique angle deposition. A substrate 50 may be positioned at an angle $\theta_B$ relative to a line L that is parallel to a crucible 52 of source material 54. $SiO_2$ may be a suitable source material. A filament 56 may be heated until it emits an electron beam that acts upon the source material to create a vapor 58 that becomes deposited on the substrate 50 in the form of rods as shown in FIG. 3.

The formed nanoporous film will generally have a refractive index less than the deposited material would have if applied in a uniform and polished layer because the air gaps provided by the pores serve to lower the effective refractive index of the film. By varying the deposition angle, the porosity of the film and therefore the refractive index of the film can be selected and adjusted almost continuously. Thus, the refractive indices of the anti-reflective assemblies formed with this process are tunable in the fabrication process.

Figure 7:
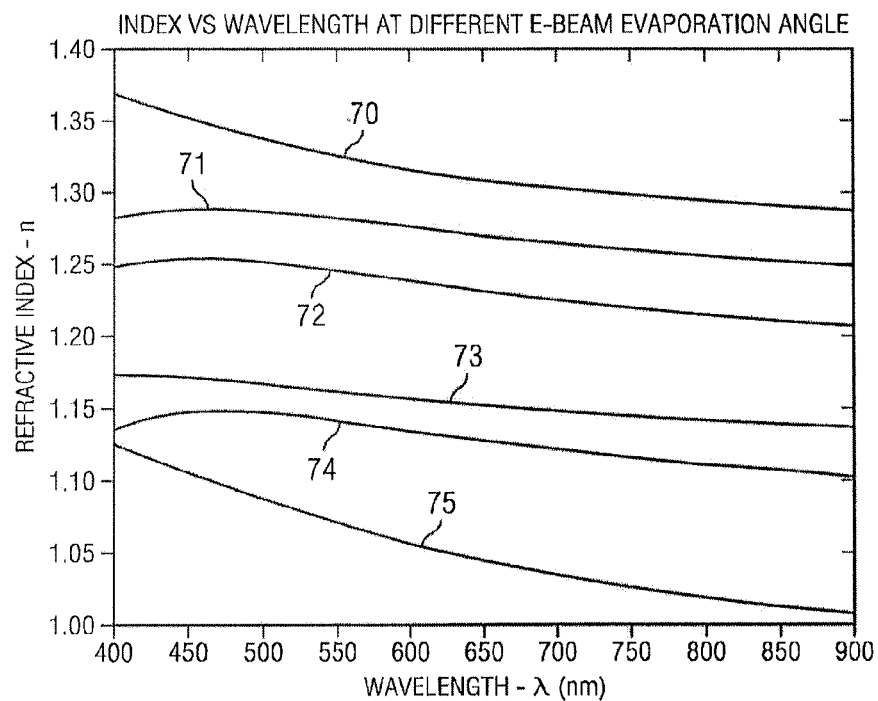
FIG. 7 is a chart describing the refractive index of assemblies formed at various evaporation angles.

FIG. 7 depicts experimental data that shows the influence that e-beam evaporation angle has on $SiO_2$ film fabricated using the above described technique. Each of the curves 70-75 represent the refractive index of $SiO_2$ film fabricated at different e-beam evaporation angles and at wavelengths ranging from 400 to 900 nm. Curve 70 is based upon a 60° evaporation angle. Curve 71 is based upon a 70° evaporation angle. Curve 72 is based upon a 75° evaporation angle. Curve 73 is based upon an 80° evaporation angle. Curve 74 is based upon a 85° evaporation angle. Curve 75 is based upon a 90° evaporation angle. As shown, when the angle between the source material plane and the substrate plane is approximately 80°, the refractive index of the film ranges from approximately 1.17 and 1.13. With larger evaporation angles, the refractive index decreases and with smaller evaporation angles, the refractive index increases.

The described technique may be used to create a single level of nanostructures, however in alternative embodiments, a closure layer may be deposited over the formed rods and a second level of rods may be formed on top of the first level. In this way, multilayer structures with even more varying refractive indices may be formed.

Figure 8:
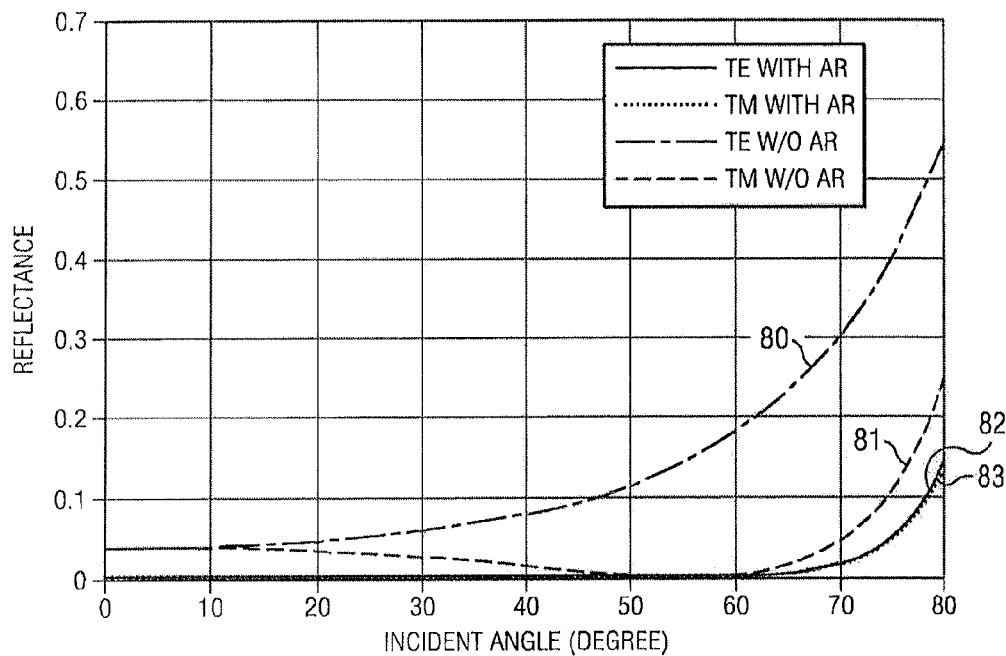
FIG. 8 is a chart describing the reflectance of the nanostructure assembly of FIG. 3.

FIG. 8 shows the calculated reflectance performance of two layers of $SiO_2$ nanoporous film fabricated using the methods described above. The two layer $SiO_2$ assembly or coating includes a 145 nm $SiO_2$ nanoporous layer (n=1.27) followed by a 223 nm $SiO_2$ nanoporous layer (n=1.05). The reflectance at a wavelength of 633 nm is less than 0.2% for angles up to 70° and less than 12% up to 80°. Similar performance may be maintained for a spectral range between 400 and 800 nm. Reflectance without the $SiO_2$ nanoporous assembly is also shown. Curve 80 represents the reflectance of a transverse electric (TE) beam with no anti-reflective assembly, and curve 81 represents the reflectance of a transverse magnetic (TM) beam with no anti-reflective assembly. Curve 82 represents the reflectance of a transverse electric (TE) beam with the two layer anti-reflective assembly described above. Curve 83 represents the reflectance of a transverse magnetic (TM) beam with the two layer anti-reflective assembly described above. The chart of FIG. 8 shows that the reflectance for both TE and TM is nearly zero at incident angles up to 70°, with the use of the anti-reflective assembly. Adding this type of broadband and large acceptance angle anti-reflective coating can reduce undesired reflection and scattering.

Figure 9:
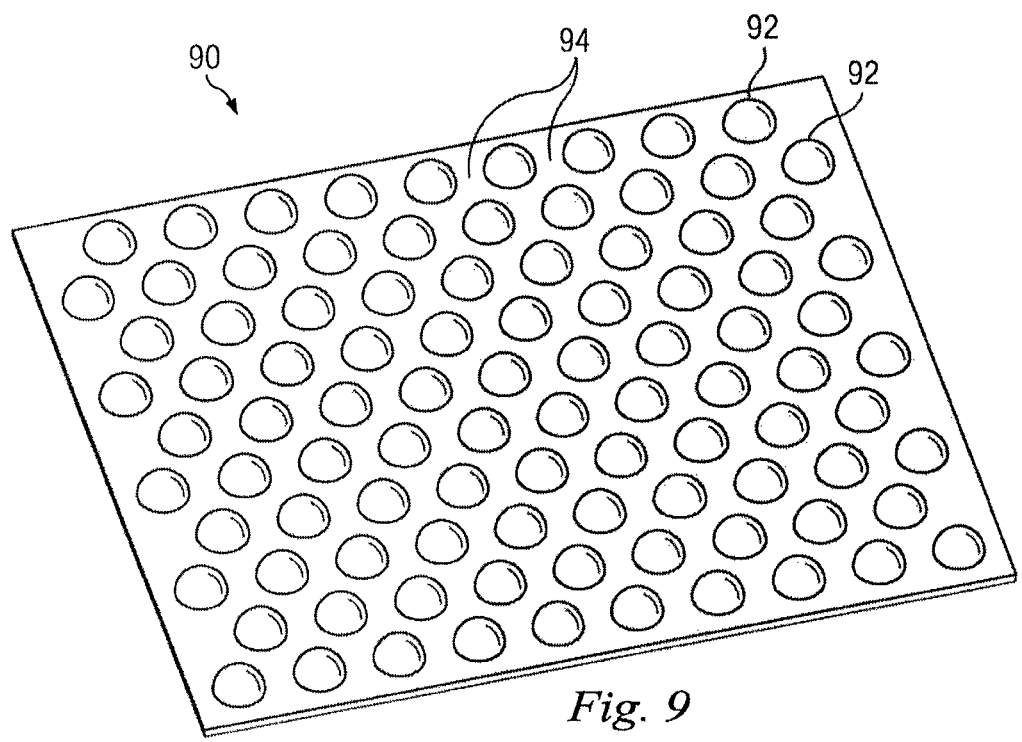
FIG. 9 is a top view of a nanostructure assembly according to another embodiment of the disclosure.
Figure 10:
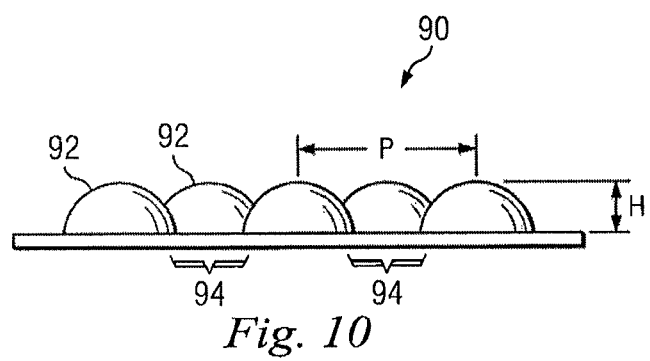
FIG. 10 is a side view of the nanostructure assembly of FIG. 9.

Referring now to FIGS. 9 and 10, in another embodiment, the anti-reflective assembly 16 may be a "moth-eye" structured assembly 90 with periodically repeating protrusions 92 and spacings 94. The assembly 90 is termed "moth-eye" because the structure is a biomimetic configuration that simulates the structure of a moth eye. The protrusions may be semispherical, conical, pyramidal, or other shape that provides a generally tapered effect. The period of the array is the distance P between the tallest points of adjacent protrusions. Although the period P may vary between adjacent protrusions, it is generally much smaller that the operating wavelength of the lens. The height H of the protrusions is also generally smaller than the operating wavelength of the lens. The effect is a gradient index distribution profile that varies between the index of the surrounding medium and the index of the substrate. Effective medium theory can be applied to calculate the average refractive index of the assembly. The gradient index profile design can be used to create a broad band and large acceptance angle anti-reflective layer.

To fabricate the moth-eye structured film, a mold is first fabricated with densely packed nano-spheres or other nanoparticles suspended on a silicon substrate. A polydimethylsiloxane (PDMS) mold is cast and may be used for subsequent stamping and replication to mass produce the moth-eye film 90. The stamping and replication may be applied either to a lens directly or to a material that may be applied to the lens. As with the embodiment of FIG. 3, the moth-eye assembly 90 has an effective lower refractive index than the unmodified lens body. Thus, the reflectivity of the lens is reduced compared to the unmodified lens body.

Figure 11:
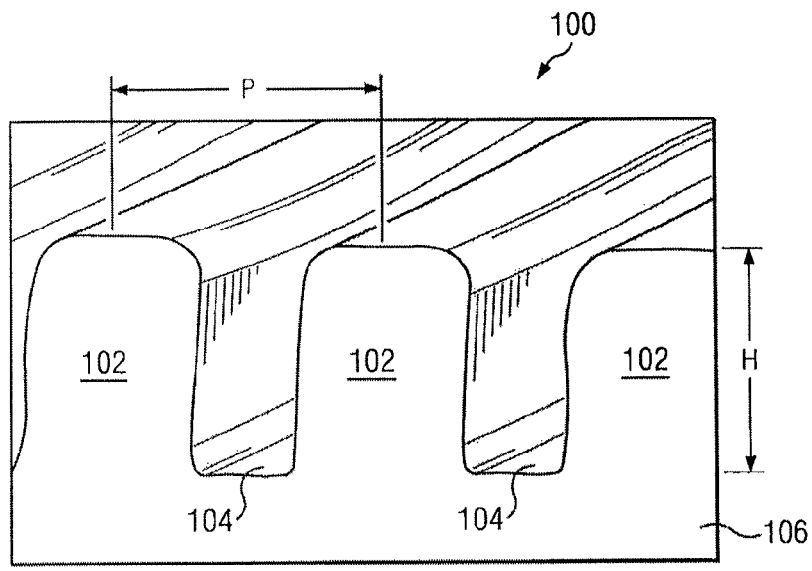
FIG. 11 is still another nanostructure assembly according to another embodiment of the disclosure.

Referring now to FIG. 11, in another embodiment, the nanostructure assembly 16 may be a grating structure 100 with elongated protrusions 102 and spacings 104 formed in a repeating pattern on a substrate 106. The protrusions may have a height H and a period P that are generally much smaller that the operating wavelength of the lens. The grating structure 100 may function as an anti-reflective coating. It may also function to couple incident light into guided modes by deflecting or refracting light in desired directions.

To fabricate the grating structure 100, one suitable technique that may be utilized is ultraviolet (UV) interference lithography. This technique may fabricate gratings over large surfaces, such as a lens, and is suitable for use on curved surfaces due to its large depth of focus. Using interference lithography, a mold, made of silicon or other material suitable for mass production, is used for subsequent stamping and replication either of a lens directly or of a material that may be applied to the lens. As with the embodiment of FIG. 3, the grating structure 100 has an effective lower refractive index than the unmodified lens body. Thus, the reflectivity of the lens is reduced compared to the unmodified lens body.

Figure 12:
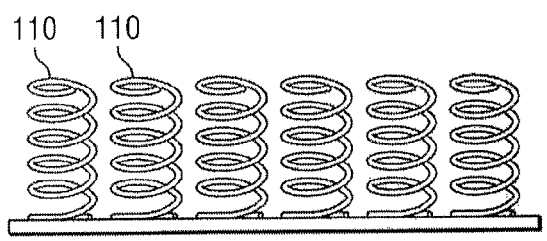
FIG. 12 is still another nanostructure assembly according to another embodiment of the disclosure.

Referring now to FIG. 12, in another embodiment, the assembly 16 may be similar the nanoporous film 29 described above, but rather than linear rods, a plurality of helical rods 110 extend from the substrate. Helical rods may be formed by rotating the substrate during the formation process, such as an oblique angle deposition process. Because the in-plane orientation of the rods 110 change continuously as the film grows, the film can be designed for reflective or anti-reflective applications.

Figure 13:
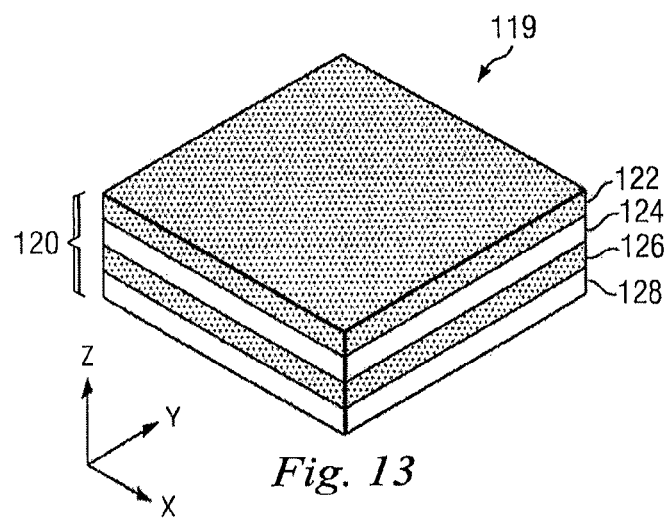
FIG. 13 depicts a portion of multi-layer film that can be formed with one of the nanostructure assemblies of the present disclosure.
Figure 14:
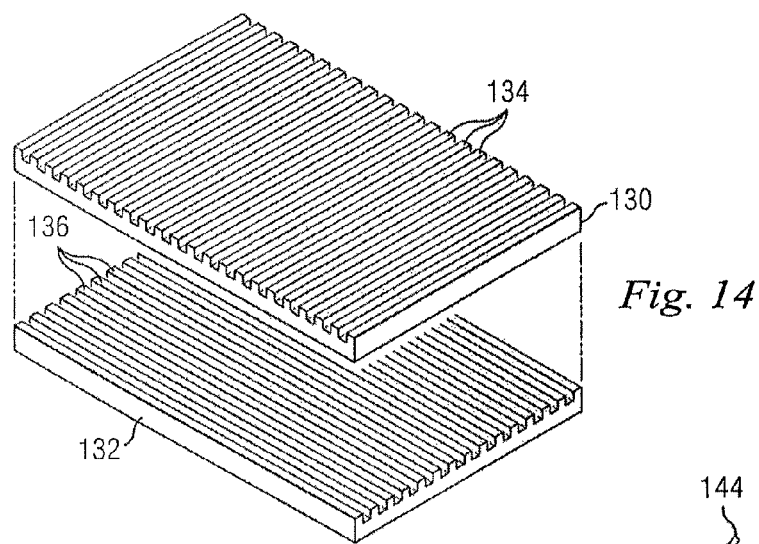
FIGS. 14 and 15 depict examples of layers that can be used in the multi-layer film of FIG. 13.
Figure 15:
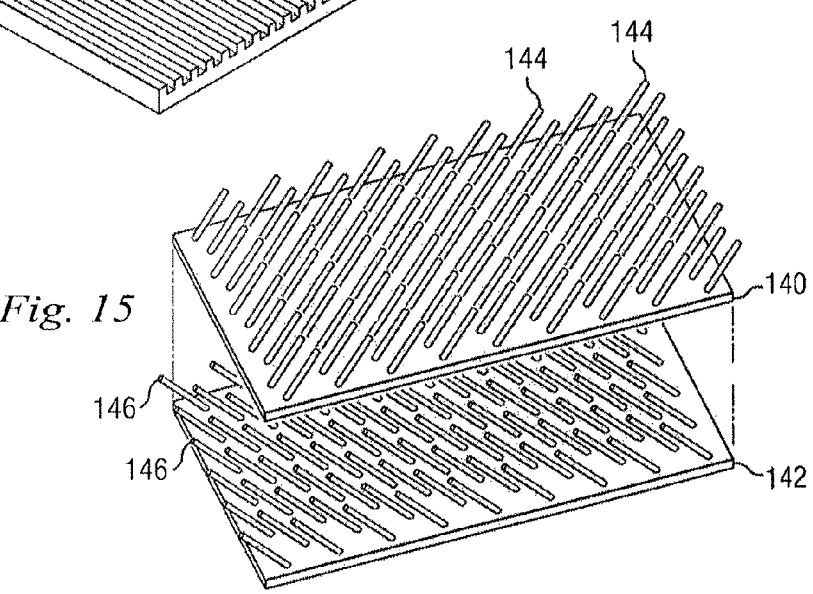

Referring now to FIG. 13, in an alternative embodiment, layers of nanostructure assemblies 120, of any of the types described above, may be arranged to effect a highly reflective multi-layer film 119. In this embodiment, each film layer 122-128 includes a nanostructure assembly 120. The layers 122-128 are birefingent and when arranged as described below form a highly reflective multi-layer film having giant birefingent optic (GBO) properties. For example, layers 122 and 126 have nanostructures oriented in the YZ plane. FIG. 14 provides an example of a layer 130 with nanostructure gratings 134 oriented in the YZ plane. FIG. 15 provides an example of a layer 140 with nanorods 144 oriented in the YZ plane. Layers 124 and 128 of the film 119 have nanostructures oriented in the XZ plane. FIG. 14 provides an example of a layer 132 with nanostructure gratings 136 oriented in the XZ plane. FIG. 15 provides an example of a layer 142 with nanorods 146 oriented in the XZ plane. Although discretely layered films have been described, in alternative embodiments, helical rods, such as those described above for FIG. 12, may be used to effect continuously changing in-plane orientation. The helical rods described above for FIG. 12 may also be used to effectively create a continuously changing in-plane orientation.

Highly reflective films formed using nanostructures may be used in applications that utilize mirrored surfaces or films. For example, mirrored optical implants, such as telescopic intraocular implants, may utilize mirrored components to effect reflection and focusing of light. U.S. Pat. No. 7,842,086, which is incorporated by reference herein in its entirety, describes mirrored intraocular implants that may suitable for use with the above described highly reflective films. In one embodiment, such an intraocular implant includes an implant body with a plurality of mirrors that receive light from a scene and focus the light onto the retina. At least one of the mirrors includes a surface that is made highly reflective through the use of the previously described nanostructure reflective films. Generally, the reflective surfaces have a reflectivity of approximately 25% or more.

Figure 16:
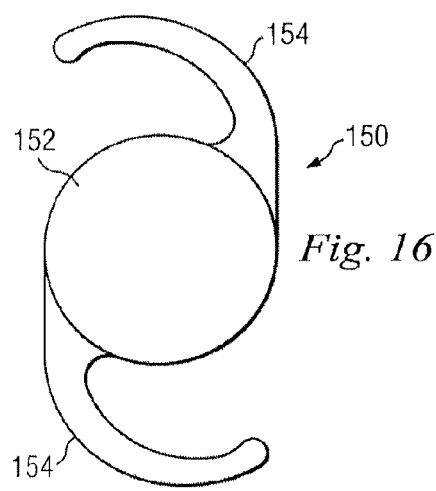
FIG. 16 is a front view of an intraocular lens provided with an anti-reflective assembly.
Figure 17:
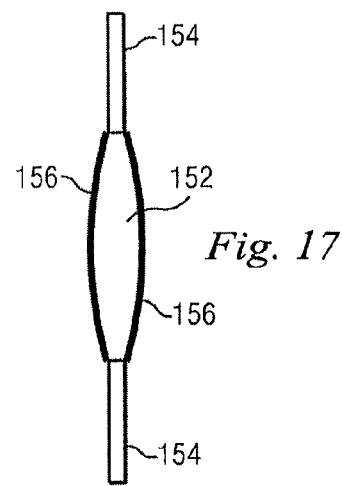
FIG. 17 is a side view of the intraocular lens of FIG. 12.

Referring now to FIGS. 16 and 17, an intraocular lens 150 is one type of ophthalmic lens that may be improved using any of the above described nanostructure assemblies 16. The intraocular lens 150 has a lens body 152 from which a pair of lens retaining haptics 154 extend. As shown more clearly in FIG. 17, a nanostructure assembly 156, of any of the types described above, may cover the surfaces of the lens body 152. It may, alternatively, be desirable to also cover the haptics or only cover a portion of the lens body. A suitable intraocular lens may have a lens body formed of silicone or of a polymer such as ACRYSOF® (trademark of Alcon, Ft. Worth, Tex.).

For intraocular lenses and other ophthalmic lenses that directly contact or are implanted in the eye, biocompatibility is important to the functionality of the lens. The variegated surfaces of the above described anti-reflective assemblies may allow for microlubrication and the movement and channeling of beneficial fluid into contact with the surrounding biologic tissue. For example, an intraocular lens interacts with the aqueous humor of the eye and the use of the assemblies 16 may permit extended wear while also reducing reflectivity of the lens.

Although several selected embodiments have been illustrated and described in detail, it will be understood that they are exemplary, and that a variety of substitutions and alterations are possible without departing from the spirit and scope of the present invention, as defined by the following claims.

We claim:

1. An ophthalmic intraocular lens system for implantation in an eye, comprising:
   an intraocular lens comprising a lens body and haptics extending therefrom, wherein the lens body comprises a curved outer surface;
   an assembly including a plurality of spaced apart nanostructures, said assembly covering at least a portion of the curved outer surface, wherein each one of said plurality of spaced apart nanostructures extends from a corresponding portion of the curved outer surface at an oblique angle with respect to the corresponding portion of the curved outer surface such that a central longitudinal axis of each one of said plurality of spaced apart nanostructures extends at an oblique angle with respect to the corresponding portion of the curved outer surface.

2. The ophthalmic lens system of claim 1 wherein a refractive index of the assembly is between 1.3 and 1.6.

3. The ophthalmic lens system of claim 1 wherein the nanostructures include nanorods.

4. The ophthalmic lens system of claim 1 wherein the nanostructures include a pattern of periodic repeating nanorods.

5. The ophthalmic lens system of claim 1 wherein the assembly is attached to the curved outer surface.

6. The ophthalmic lens system of claim 1 wherein the assembly is integrally formed with the curved outer surface.

7. The ophthalmic lens system of claim 1 wherein the plurality of nanostructures include an array of nanorods and spacings wherein the spacings are adapted to receive a fluid.

8. The ophthalmic lens system of claim 1 wherein the plurality of nanostructures are formed from $SiO_2$.

9. The ophthalmic lens system of claim 1 wherein a refractive index of the curved outer surface is greater than the refractive index of the assembly.

10. The ophthalmic lens system of claim 1 wherein the plurality of nanostructures comprises a first layer and wherein the assembly further comprises a second layer at least partially covering the first layer, the second layer including another plurality of nanostructures.

11. The ophthalmic lens system of claim 1 wherein the curved outer surface has a first reflectance and the assembly has a second reflectance.

12. The ophthalmic lens system of claim 11 wherein the first reflectance is greater than the second reflectance.

13. The ophthalmic lens system of claim 11 wherein the first reflectance is less than the second reflectance.

14. An intraocular lens system for implantation in an eye, comprising:
   an intraocular lens comprising a lens body and haptics extending therefrom, wherein the lens body comprises a curved surface having a first surface reflectance;
   an assembly including a plurality of spaced apart nanoprojections, each one of said plurality of nanoprojections extending from a corresponding portion of the curved surface at an oblique angle with respect to the corresponding portion of the curved surface such that a central longitudinal axis of each one of said plurality of nanoprojections extends at an oblique angle with respect to the corresponding portion of the curved surface, said assembly covering at least a portion of the curved surface, wherein the covered portion has a second surface reflectance lower than the first surface reflectance.

15. The ophthalmic lens system of claim 14 wherein the nanoprojections extend in different directions.

16. The ophthalmic lens system of claim 14 wherein the nanoprojections are arranged in first and second layers.

17. The ophthalmic lens system of claim 14 wherein the curved surface is an outer curved surface.

18. The ophthalmic lens system of claim 14 wherein the curved surface is an interior curved surface.

19. The ophthalmic lens system of claim 14 wherein the nanoprojections are deposited on the curved surface.

20. The ophthalmic lens system of claim 14 wherein the nanoprojections are etched in the curved surface.

21. The ophthalmic lens system of claim 14 wherein the curved surface has a first lubricity and the covered portion has a second lubricity greater than the first lubricity.

22. The ophthalmic lens system of claim 14 wherein the curved surface has a first surface scattering property and the covered portion has a second surface scattering property that is less than the first surface scattering property.

23. The ophthalmic lens system of claim 1, wherein the assembly comprises a nanoporous film.

24. The ophthalmic lens system of claim 14, wherein the assembly covers the haptics.

25. The ophthalmic lens system of claim 14, wherein the assembly comprises a nanoporous film.

* * * * *